(12) United States Patent
De Mesmaeker et al.

(10) Patent No.: US 11,039,613 B2
(45) Date of Patent: Jun. 22, 2021

(54) GERMINATION PROMOTERS

(71) Applicant: SYNGENTA PARTICIPATIONS AG, Basel (CH)

(72) Inventors: Alain De Mesmaeker, Stein (CH); Claudio Screpanti, Stein (CH); Alexandre Franco Jean Camille Lumbroso, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 16/485,136

(22) PCT Filed: Feb. 1, 2018

(86) PCT No.: PCT/EP2018/052462
§ 371 (c)(1),
(2) Date: Aug. 9, 2019

(87) PCT Pub. No.: WO2018/145979
PCT Pub. Date: Aug. 16, 2018

(65) Prior Publication Data
US 2019/0380339 A1 Dec. 19, 2019

(30) Foreign Application Priority Data
Feb. 9, 2017 (GB) ..................... 1702158

(51) Int. Cl.
*A01N 43/38* (2006.01)
*C07D 403/12* (2006.01)
*C07D 405/12* (2006.01)

(52) U.S. Cl.
CPC .......... *A01N 43/38* (2013.01); *C07D 403/12* (2013.01); *C07D 405/12* (2013.01)

(58) Field of Classification Search
None
See application file for complete search history.

(56) References Cited

FOREIGN PATENT DOCUMENTS

| WO | 2013139949 A1 | 9/2013 |
| WO | 2015128321 A1 | 9/2015 |

OTHER PUBLICATIONS

International Search Report & Written Opinion for PCT/EP2018/052462, dated Apr. 5, 2018.
F.-D. Boyer et al, "Structure-Activity Relationship Studies of Strigolactone-Related Molcules for Branching Inhibition in Garden Pea: Molecule Design for Shoot Branching", Plant Physiology, vol. 159, No. 4, Aug. 1, 2012, pp. 1524-1544.

*Primary Examiner* — Alton N Pryor
(74) *Attorney, Agent, or Firm* — Baker & Hostetler LLP; Toni-Junell Herbert

(57) ABSTRACT

The present invention relates to new compounds of formula (I) for the promotion of seed germination, to processes for preparing the compounds, to seeds comprising the compounds, to seed germination promoting compositions comprising the compounds and to methods of using the compounds for promoting the germination of seeds. In particular, the compounds are useful in promoting germination of corn under cold stress conditions.

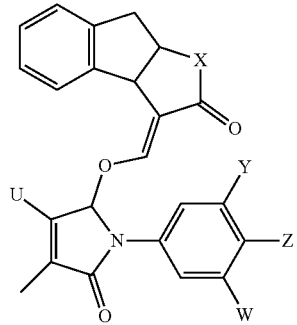

20 Claims, No Drawings

GERMINATION PROMOTERS

CROSS-REFERENCE TO RELATED APPLICATIONS

This application is a 371 National Stage application of International Application No. PCT/EP2018/052462, filed Feb. 1, 2018, which claims priority to GB 1702158.5 filed Feb. 9, 2017, the entire contents of which applications are hereby incorporated by reference.

The present invention relates to new compounds for the promotion of seed germination, to processes for preparing the compounds, to seeds comprising the compounds, to seed germination promoting compositions comprising the compounds and to methods of using the compounds for promoting the germination of seeds. In particular, the compounds are useful in promoting germination of corn under various stress conditions.

The compounds of the present invention are derivatives of strigolactone. Strigolactone derivatives are phytohormones which may have plant growth regulation and seed germination properties. They have previously been described in the literature. Certain known strigolactam derivatives may have properties analogous to strigolactones, e.g., plant growth regulation and/or seed germination promotion. WO2015/061764 discloses plant propagation materials comprising chemical mimics of strigolactone thought to be particularly effective under drought stress conditions. WO2015/128321 describes strigolactone derivatives with a modified butenolide ring.

The present invention relates to strigolactone derivatives that have improved properties. Benefits of the compounds of the present invention include improved tolerance to abiotic stress, improved seed germination, better regulation of crop growth, improved crop yield, and/or improved physical properties such as chemical, hydrolytic, physical and/or soil stability. In particular, improved germination may include faster germination, more uniform germination, more synchronous germination or higher percentage of seeds that germinate. Compounds of the present invention may also improve germination under abiotic stress conditions, such as mild drought stress, drought stress, cold stress, salt stress or osmotic stress.

According to the present invention, there is provided a compound of formula (I)

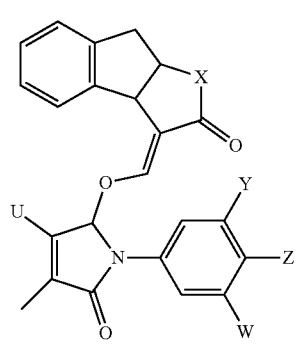

(I)

wherein X is oxygen or N—R$^1$;

R$^1$ is selected from the group consisting of hydrogen, C$_1$-C$_6$ alkyl, C$_3$-C$_6$ cycloalkyl, C$_2$-C$_6$ alkenyl, C$_2$-C$_6$ alkynyl, C$_1$-C$_8$ alkylcarbonyl, C$_1$-C$_8$ alkoxycarbonyl, aryl, heteroaryl, heterocyclyl and benzyl each optionally substituted with one or more R$^2$;

each R$^2$ is independently selected from the group consisting of halogen, cyano, C$_1$-C$_4$ alkyl, C$_1$-C$_4$ haloalkyl, C$_1$-C$_4$ alkoxy, C$_1$-C$_4$ haloalkoxy, C$_1$-C$_4$ alkylcarbonyl, C$_1$-C$_4$ alkoxycarbonyl, carboxylic acid, aminocarbonyl, C$_1$-C$_4$ aminocarbonyl and C$_3$-C$_4$ cycloalkyl;

W, Y and Z are each independently hydrogen, methyl, trifluoromethyl or fluorine; and U is hydrogen or methyl;

or salts thereof.

The compounds of the present invention may exist in different geometric or optical isomers (diastereoisomers and enantiomers) or tautomeric forms. This invention covers all such isomers and tautomers and mixtures thereof in all proportions as well as isotopic forms such as deuterated compounds. The invention also covers all salts, N-oxides, and metalloidic complexes of the compounds of the present invention.

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups include C$_1$-C$_6$ alkyl, C$_1$-C$_4$ alkyl, and C$_1$-C$_3$ alkyl.

The term "alkenyl", as used herein, is an alkyl moiety having at least one carbon-carbon double bond, for example C$_2$-C$_6$ alkenyl. Specific examples include vinyl and allyl. The alkenyl moiety may be part of a larger group (such as alkenoxy, alkenoxy-carbonyl, alkenylcarbonyl, alkyenlaminocarbonyl, dialkenylaminocarbonyl).

The term "acetoxy" refers to —OC(=O)CH$_3$.

The term "alkynyl", as used herein, is an alkyl moiety having at least one carbon-carbon triple bond, for example C$_2$-C$_6$ alkynyl. Specific examples include ethynyl and propargyl. The alkynyl moiety may be part of a larger group (such as alkynoxy, alkynoxycarbonyl, alkynylcarbonyl, alkynylaminocarbonyl, dialkynylaminocarbonyl).

Halogen is fluorine (F), chlorine (Cl), bromine (Br) or iodine (I).

Haloalkyl groups (either alone or as part of a larger group, such as haloalkoxy or haloalkylthio) are alkyl groups which are substituted with one or more of the same or different halogen atoms and are, for example, —CF$_3$, —CF$_2$C$_1$, —CH$_2$CF$_3$ or —CH$_2$CHF$_2$.

Hydroxyalkyl groups are alkyl groups which are substituted with one or more hydroxyl group and are, for example, —CH$_2$OH, —CH$_2$CH$_2$OH or —CH(OH)CH$_3$.

Alkoxyalkyl groups are an alkoxy group bonded to an alkyl (R—O—R'), for example —(CH$_2$)rO(CH$_2$)sCH$_3$, wherein r is 1 to 6 and s is 1 to 5.

In the context of the present specification the term "aryl" refers to a ring system which may be mono, bi or tricyclic. Examples of such rings include phenyl, naphthalenyl, anthracenyl, indenyl or phenanthrenyl.

Unless otherwise indicated, alkenyl and alkynyl, on their own or as part of another substituent, may be straight or branched chain and may contain 2 to 6 carbon atoms, and where appropriate, may be in either the (E) or (Z) configuration. Examples include vinyl, allyl, ethynyl and propargyl.

Unless otherwise indicated, cycloalkyl may be mono- or bi-cyclic, may be optionally substituted by one or more C$_1$-C$_6$ alkyl groups, and contain 3 to 7 carbon atoms. Examples of cycloalkyl include cyclopropyl, 1-methylcyclopropyl, 2-methylcyclopropyl, cyclobutyl, cyclopentyl and cyclohexyl.

The term "heterocyclyl" refers to a ring system containing from one to four heteroatoms selected from N, O and S, wherein the nitrogen and sulphur atoms are optionally oxidized, and the nitrogen atom(s) are optionally quaternized. Heterocyclyl includes heteroaryl, saturated analogs, and in addition their unsaturated or partially unsaturated analogues such as 4,5,6,7-tetrahydro-benzothiophenyl, 9H-fluorenyl, 3,4-dihydro-2H-benzo-1,4-dioxepinyl, 2,3-dihydro-benzo¬furanyl, piperidinyl, 1,3-dioxolanyl, 1,3-dioxanyl, 4,5-dihydro-isoxazolyl, tetrahydrofuranyl and morpholinyl. In addition, the term "heterocyclyl" includes heterocycloalkyl, a non-aromatic monocyclic or polycyclic ring comprising carbon and hydrogen atoms and at least one heteroatom selected from nitrogen, oxygen, and sulfur such asoxetanyl or thietanyl. A monocyclic heterocycloalkyl may contain 3 to 7 members.

The term "heteroaryl" refers to an aromatic ring system containing from one to four heteroatoms selected from N, O, and S, wherein the nitrogen and sulfur atoms are optionally oxidized, for example having 5, 6, 9 or 10 members, and consisting either of a single ring or of two or more fused rings. Single rings may contain up to three heteroatoms, and bicyclic systems up to four heteroatoms, which will preferably be chosen from nitrogen, oxygen and sulfur. Examples of such groups include pyridyl, pyridazinyl, pyrimidinyl, pyrazinyl, furanyl, thienyl, oxazolyl, isoxazolyl, oxadiazolyl, thiazolyl, isothiazolyl, thiadiazolyl, pyrrolyl, pyrazolyl, imidazolyl, triazolyl and tetrazolyl.

Further definitions of X, $R^1$, $R^2$, U, W, Y and Z and are, in any combination, as set out below.

X is oxygen or N—$R^1$. In one embodiment, X is oxygen. In a further embodiment, X is N—R1.

$R^1$ is selected from the group consisting of hydrogen, $C_1$-$C_6$ alkyl, $C_3$-$C_6$ cycloalkyl, $C_2$-$C_6$ alkenyl, $C_2$-$C_6$ alkynyl, $C_1$-$C_8$ alkylcarbonyl, $C_1$-$C_8$ alkoxycarbonyl, aryl, heteroaryl, heterocyclyl and benzyl each optionally substituted with one or more $R^2$.

When $R^1$ is $C_1$-$C_6$ alkyl, $C_3$-$C_6$ cycloalkyl, $C_2$-$C_6$ alkenyl, $C_2$-$C_6$ alkynyl, $C_1$-$C_8$ alkylcarbonyl, $C_1$-$C_8$ alkoxycarbonyl, aryl, heteroaryl, heterocyclyl or benzyl each of these may be substituted with 0, 1, 2, 3 or 4 $R^2$ groups. In one embodiment, when $R^1$ is $C_1$-$C_6$ alkyl, $C_3$-$C_6$ cycloalkyl, $C_2$-$C_6$ alkenyl, $C_2$-$C_6$ alkynyl, $C_1$-$C_8$ alkylcarbonyl, $C_1$-$C_8$ alkoxycarbonyl, aryl, heteroaryl, heterocyclyl or benzyl each of these may be substituted with 0, 1 or 2 $R^2$ groups.

In one embodiment, $R^1$ is selected from the group consisting of hydrogen and $C_1$-$C_4$ alkyl, $C_4$ alkylcarbonyl, $C_1$-$C_6$ alkoxycarbonyl and heteroaryl each optionally substituted with one or more $R^2$.

Each $R^2$ is independently selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylcarbonyl, $C_1$-$C_4$ alkoxycarbonyl, carboxylic acid, aminocarbonyl, $C_1$-$C_4$ aminocarbonyl and $C_3$-$C_4$ cycloalkyl.

In one embodiment, each $R^2$ is independently selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, and $C_3$-$C_4$ cycloalkyl.

In a further embodiment, each $R^2$ is independently selected from the group consisting of halogen, cyano and $C_3$-$C_4$ cycloalkyl. In one embodiment, $R^2$ is halogen.

U is hydrogen or methyl. In one embodiment U is hydrogen. In a further embodiment U is methyl.

W, Y and Z are each independently hydrogen, methyl, trifluoromethyl or fluorine. In one embodiment, W, Y and Z are each independently hydrogen or trifluoromethyl.

W is hydrogen, methyl, trifluoromethyl or fluorine. In one embodiment, W is hydrogen, fluorine or trifluoromethyl. In one embodiment, W is fluorine or trifluoromethyl. In one embodiment, W is hydrogen or trifluoromethyl. In one embodiment W is hydrogen. In one embodiment, W is fluorine. In a further embodiment, W is methyl. In a further embodiment, W is trifluoromethyl.

Y is hydrogen, methyl, trifluoromethyl or fluorine. In one embodiment, Y is hydrogen, fluorine or trifluoromethyl. In one embodiment, Y is fluorine or trifluoromethyl. In one embodiment, Y is hydrogen or trifluoromethyl. In one embodiment Y is hydrogen. In another embodiment, Y is fluorine. In a further embodiment, Y is methyl. In a further embodiment, Y is trifluoromethyl.

Z is hydrogen, methyl, trifluoromethyl or fluorine. In one embodiment, Z is hydrogen, fluorine or methyl. In one embodiment, Z is hydrogen or fluorine. In one embodiment Z is hydrogen. In another embodiment, Z is fluorine. In a further embodiment, Z is methyl. In a further embodiment, Z is trifluoromethyl.

Preferably W and Y are each independently selected from the group consisting of trifluoromethyl, and fluorine and methyl, Z is fluorine or hydrogen. Preferably W and Y are both trifluoromethyl, Z is fluorine or hydrogen and U is hydrogen.

In one embodiment, W and Y are both trifluoromethyl.

In one embodiment the compound of the present invention is formula (II):

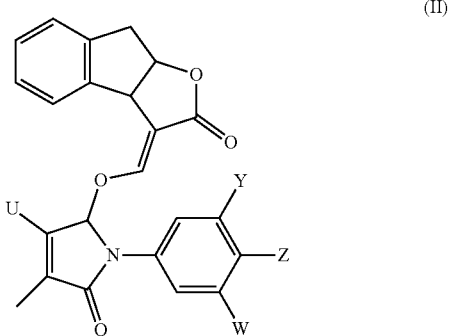

(II)

In a further embodiment the compound of the present invention is formula (III):

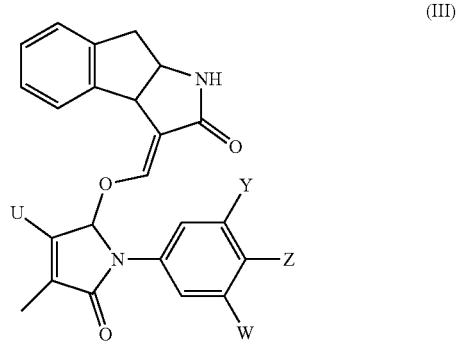

(III)

For example, the present invention includes the following compounds:

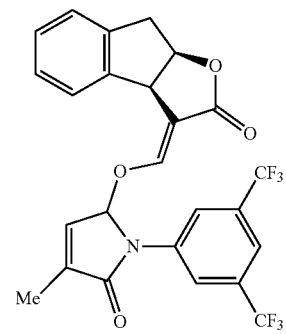
(II-1)

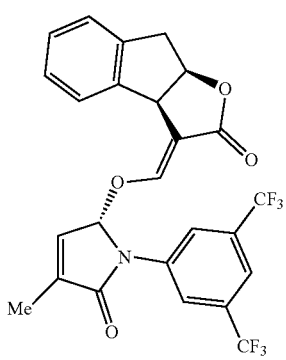
(II-1a)

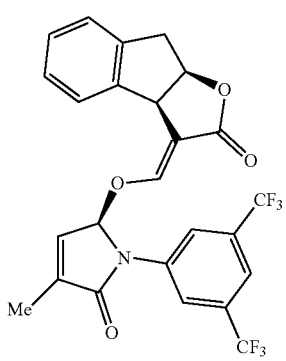
(II-1b)

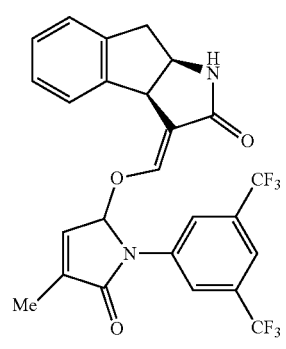
(III-1)

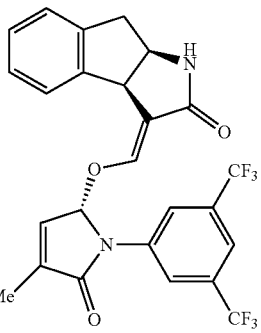
(III-1a)

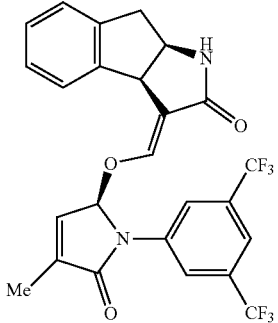
(III-1b)

Table 1 below includes examples of compounds of the present invention.

TABLE 1

Compounds of Invention

| Compound | X | W | Y | Z | U |
|---|---|---|---|---|---|
| I-1 | N—C(O)OtBu | CF$_3$ | CF$_3$ | H | H |
| I-2 | N—C(O)OtBu | H | H | H | H |
| I-3 | N—C(O)OtBu | H | CF$_3$ | H | H |
| I-4 | N—C(O)OtBu | H | H | CF$_3$ | H |
| I-5 | N—C(O)OtBu | F | F | H | H |
| I-6 | N—C(O)OtBu | H | H | F | H |
| I-7 | N—C(O)OtBu | F | F | F | H |
| I-8 | N—C(O)OtBu | F | F | CF$_3$ | H |
| I-9 | N—C(O)OtBu | Me | F | F | H |
| I-10 | N—C(O)OtBu | F | F | Me | H |
| I-11 | N—C(O)OtBu | Me | Me | CF$_3$ | H |
| I-12 | N—C(O)OtBu | H | Me | CF$_3$ | H |
| I-13 | N—C(O)OtBu | CF$_3$ | Me | H | H |
| I-14 | N—C(O)OtBu | H | H | Me | H |
| I-15 | N—Me | CF$_3$ | CF$_3$ | H | H |
| I-16 | N—Me | H | H | H | H |
| I-17 | N—Me | H | CF$_3$ | H | H |
| I-18 | N—Me | H | H | CF$_3$ | H |
| I-19 | N—Me | F | F | H | H |
| I-20 | N—Me | H | H | F | H |

TABLE 1-continued

Compounds of Invention

| Compound | X | W | Y | Z | U |
|---|---|---|---|---|---|
| I-21 | N—Me | F | F | F | H |
| I-22 | N—Me | F | F | CF₃ | H |
| I-23 | N—Me | Me | F | F | H |
| I-24 | N—Me | F | F | Me | H |
| I-25 | N—Me | Me | Me | CF₃ | H |
| I-26 | N—Me | H | Me | CF₃ | H |
| I-27 | N—Me | CF₃ | Me | H | H |
| I-28 | N—Me | H | H | Me | H |
| II-1 | O | CF₃ | CF₃ | H | H |
| II-2 | O | H | H | H | H |
| II-3 | O | H | CF₃ | H | H |
| II-4 | O | H | H | CF₃ | H |
| II-5 | O | F | F | H | H |
| II-6 | O | H | H | F | H |
| II-7 | O | F | F | F | H |
| II-8 | O | F | F | CF₃ | H |
| II-9 | O | Me | F | F | H |
| II-10 | O | F | F | Me | H |
| II-11 | O | Me | Me | CF₃ | H |
| II-12 | O | H | Me | CF₃ | H |
| II-13 | O | CF₃ | Me | H | H |
| II-14 | O | H | H | Me | H |
| III-1 | NH | CF₃ | CF₃ | H | H |
| III-2 | NH | H | H | H | H |
| III-3 | NH | H | CF₃ | H | H |
| III-4 | NH | H | H | CF₃ | H |
| III-5 | NH | F | F | H | H |
| III-6 | NH | H | H | F | H |
| III-7 | NH | F | F | F | H |
| III-8 | NH | F | F | CF₃ | H |
| III-9 | NH | Me | F | F | H |
| III-10 | NH | F | F | Me | H |
| III-11 | NH | Me | Me | CF₃ | H |
| III-12 | NH | H | Me | CF₃ | H |
| III-13 | NH | CF₃ | Me | H | H |
| III-14 | NH | H | H | Me | H |
| I-29 | N—C(O)OtBu | CF₃ | CF₃ | H | Me |
| I-30 | N—C(O)OtBu | H | H | H | Me |
| I-31 | N—C(O)OtBu | H | CF₃ | H | Me |
| I-32 | N—C(O)OtBu | H | H | CF₃ | Me |
| I-33 | N—C(O)OtBu | F | F | H | Me |
| I-34 | N—C(O)OtBu | H | H | F | Me |
| I-35 | N—C(O)OtBu | F | F | F | Me |
| I-36 | N—C(O)OtBu | F | F | CF₃ | Me |
| I-37 | N—C(O)OtBu | Me | F | F | Me |
| I-38 | N—C(O)OtBu | F | F | Me | Me |
| I-39 | N—C(O)OtBu | Me | Me | CF₃ | Me |
| I-40 | N—C(O)OtBu | H | Me | CF₃ | Me |
| I-41 | N—C(O)OtBu | CF₃ | Me | H | Me |
| I-42 | N—C(O)OtBu | H | H | Me | Me |
| III-15 | NH | CF₃ | CF₃ | H | Me |
| III-16 | NH | H | H | H | Me |
| III-17 | NH | H | CF₃ | H | Me |
| III-18 | NH | H | H | CF₃ | Me |
| III-19 | NH | F | F | H | Me |
| III-20 | NH | H | H | F | Me |
| III-21 | NH | F | F | F | Me |
| III-22 | NH | F | F | CF₃ | Me |
| III-23 | NH | Me | F | F | Me |
| III-24 | NH | F | F | Me | Me |
| III-25 | NH | Me | Me | CF₃ | Me |
| III-26 | NH | H | Me | CF₃ | Me |
| III-27 | NH | CF₃ | Me | H | Me |
| III-28 | NH | H | H | Me | Me |
| I-43 | N—Me | CF₃ | CF₃ | H | Me |
| I-44 | N—Me | H | H | H | Me |
| I-45 | N—Me | H | CF₃ | H | Me |
| I-46 | N—Me | H | H | CF₃ | Me |
| I-47 | N—Me | F | F | H | Me |
| I-48 | N—Me | H | H | F | Me |
| I-49 | N—Me | F | F | F | Me |
| I-50 | N—Me | F | F | CF₃ | Me |
| I-51 | N—Me | Me | F | F | Me |
| I-52 | N—Me | F | F | Me | Me |
| I-53 | N—Me | Me | Me | CF₃ | Me |
| I-54 | N—Me | H | Me | CF₃ | Me |
| I-55 | N—Me | CF₃ | Me | H | Me |
| I-56 | N—Me | H | H | Me | Me |
| I-57 | N—C(O)Me | CF₃ | CF₃ | H | Me |
| I-58 | N—C(O)Me | H | H | H | Me |
| I-59 | N—C(O)Me | H | CF₃ | H | Me |
| I-60 | N—C(O)Me | H | H | CF₃ | Me |
| I-61 | N—C(O)Me | F | F | H | Me |
| I-62 | N—C(O)Me | H | H | F | Me |
| I-63 | N—C(O)Me | F | F | F | Me |
| I-64 | N—C(O)Me | F | F | CF₃ | Me |
| I-65 | N—C(O)Me | Me | F | F | Me |
| I-66 | N—C(O)Me | F | F | Me | Me |
| I-67 | N—C(O)Me | Me | Me | CF₃ | Me |
| I-68 | N—C(O)Me | H | Me | CF₃ | Me |
| I-69 | N—C(O)Me | CF₃ | Me | H | Me |
| I-70 | N—C(O)Me | H | H | Me | Me |
| I-71 | N—C(O)Me | CF₃ | CF₃ | H | H |
| I-72 | N—C(O)Me | H | H | H | H |
| I-73 | N—C(O)Me | H | CF₃ | H | H |
| I-74 | N—C(O)Me | H | H | CF₃ | H |
| I-75 | N—C(O)Me | F | F | H | H |
| I-76 | N—C(O)Me | H | H | F | H |
| I-77 | N—C(O)Me | F | F | F | H |
| I-78 | N—C(O)Me | F | F | CF₃ | H |
| I-79 | N—C(O)Me | Me | F | F | H |
| I-80 | N—C(O)Me | F | F | Me | H |
| I-81 | N—C(O)Me | Me | Me | CF₃ | H |
| I-82 | N—C(O)Me | H | Me | CF₃ | H |
| I-83 | N—C(O)Me | CF₃ | Me | H | H |
| I-84 | N—C(O)Me | H | H | Me | H |
| II-15 | O | CF₃ | CF₃ | H | Me |
| II-16 | O | H | H | H | Me |
| II-17 | O | H | CF₃ | H | Me |
| II-18 | O | H | H | CF₃ | Me |
| II-19 | O | F | F | H | Me |
| II-20 | O | H | H | F | Me |
| II-21 | O | F | F | F | Me |
| II-22 | O | F | F | CF₃ | Me |
| II-23 | O | Me | F | F | Me |
| II-24 | O | F | F | Me | Me |
| II-25 | O | Me | Me | CF₃ | Me |
| II-26 | O | H | Me | CF₃ | Me |

TABLE 1-continued

Compounds of Invention

| Compound | X | W | Y | Z | U |
|---|---|---|---|---|---|
| II-27 | O | CF$_3$ | Me | H | Me |
| II-28 | O | H | H | Me | Me |

Me = methyl
tBu = tert-butyl

In one embodiment, the compounds of the present invention are applied in combination with an agriculturally acceptable adjuvant. In particular, there is provided a composition comprising a compound of the present invention and an agriculturally acceptable adjuvant. There may also be mentioned an agrochemical composition comprising a compound of the present invention.

The present invention provides a method of improving the tolerance of a plant to abiotic stress, wherein the method comprises applying to the plant, plant part, plant propagation material, or plant growing locus a compound, composition or mixture according to the present invention. In one embodiment the abiotic stress is cold, salt and/or osmotic stress.

The present invention provides a method for regulating or improving the growth of a plant, wherein the method comprises applying to the plant, plant part, plant propagation material, or plant growing locus a compound, composition or mixture according to the present invention. In one embodiment, plant growth is regulated or improved when the plant is subject to abiotic stress conditions.

The present invention also provides a method for promoting seed germination or emergence of a plant, comprising applying to the seed, or a locus containing seeds, a compound, composition or mixture according to the present invention. Germination or emergence are stimulated, for example through faster or more uniform germination or emergence.

The present invention also provides a method for safening a plant against phytotoxic effects of chemicals, comprising applying to the plant, plant part, plant propagation material, or plant growing locus a compound, composition or mixture according to the present invention.

Suitably the compound or composition is applied in an amount sufficient to elicit the desired response.

According to the present invention, "regulating or improving the growth of a crop" means an improvement in plant vigour, an improvement in plant quality, improved tolerance to stress factors, and/or improved input use efficiency.

An 'improvement in plant vigour' means that certain traits are improved qualitatively or quantitatively when compared with the same trait in a control plant which has been grown under the same conditions in the absence of the method of the invention. Such traits include, but are not limited to, early and/or improved germination, improved emergence, the ability to use less seeds, increased root growth, a more developed root system, increased root nodulation, increased shoot growth, increased tillering, stronger tillers, more productive tillers, increased or improved plant stand, less plant verse (lodging), an increase and/or improvement in plant height, an increase in plant weight (fresh or dry), bigger leaf blades, greener leaf colour, increased pigment content, increased photosynthetic activity, earlier flowering, longer panicles, early grain maturity, increased seed, fruit or pod size, increased pod or ear number, increased seed number per pod or ear, increased seed mass, enhanced seed filling, less dead basal leaves, delay of senescence, improved vitality of the plant, increased levels of amino acids in storage tissues and/or less inputs needed (e.g. less fertiliser, water and/or labour needed). A plant with improved vigour may have an increase in any of the aforementioned traits or any combination or two or more of the aforementioned traits.

An 'improvement in plant quality' means that certain traits are improved qualitatively or quantitatively when compared with the same trait in a control plant which has been grown under the same conditions in the absence of the method of the invention. Such traits include, but are not limited to, improved visual appearance of the plant, reduced ethylene (reduced production and/or inhibition of reception), improved quality of harvested material, e.g. seeds, fruits, leaves, vegetables (such improved quality may manifest as improved visual appearance of the harvested material), improved carbohydrate content (e.g. increased quantities of sugar and/or starch, improved sugar acid ratio, reduction of reducing sugars, increased rate of development of sugar), improved protein content, improved oil content and composition, improved nutritional value, reduction in anti-nutritional compounds, improved organoleptic properties (e.g. improved taste) and/or improved consumer health benefits (e.g. increased levels of vitamins and anti-oxidants)), improved post-harvest characteristics (e.g. enhanced shelf-life and/or storage stability, easier processability, easier extraction of compounds), more homogenous crop development (e.g. synchronised germination, flowering and/or fruiting of plants), and/or improved seed quality (e.g. for use in following seasons). A plant with improved quality may have an increase in any of the aforementioned traits or any combination or two or more of the aforementioned traits.

An 'improved tolerance to stress factors' means that certain traits are improved qualitatively or quantitatively when compared with the same trait in a control plant which has been grown under the same conditions in the absence of the method of the invention. Such traits include, but are not limited to, an increased tolerance and/or resistance to biotic and/or abiotic stress factors, and in particular abiotic stress factors which cause sub-optimal growing conditions such as drought (e.g. any stress which leads to a lack of water content in plants, a lack of water uptake potential or a reduction in the water supply to plants), cold exposure, heat exposure, osmotic stress, UV stress, flooding, increased salinity (e.g. in the soil), increased mineral exposure, ozone exposure, high light exposure and/or limited availability of nutrients (e.g. nitrogen and/or phosphorus nutrients). A plant with improved tolerance to stress factors may have an increase in any of the aforementioned traits or any combination or two or more of the aforementioned traits. In the case of drought and nutrient stress, such improved tolerances may be due to, for example, more efficient uptake, use or retention of water and nutrients. In particular, the compounds or compositions of the present invention are useful to improve tolerance to drought stress.

An 'improved input use efficiency' means that the plants are able to grow more effectively using given levels of inputs compared to the grown of control plants which are grown under the same conditions in the absence of the method of the invention. In particular, the inputs include, but are not limited to fertiliser (such as nitrogen, phosphorous, potassium, micronutrients), light and water. A plant with improved input use efficiency may have an improved use of any of the aforementioned inputs or any combination of two or more of the aforementioned inputs.

Other effects of regulating or improving the growth of a crop include a decrease in plant height, or reduction in tillering, which are beneficial features in crops or conditions where it is desirable to have less biomass and fewer tillers.

Any or all of the above crop enhancements may lead to an improved yield by improving e.g. plant physiology, plant growth and development and/or plant architecture. In the context of the present invention 'yield' includes, but is not limited to, (i) an increase in biomass production, grain yield, starch content, oil content and/or protein content, which may result from (a) an increase in the amount produced by the plant per se or (b) an improved ability to harvest plant matter, (ii) an improvement in the composition of the harvested material (e.g. improved sugar acid ratios, improved oil composition, increased nutritional value, reduction of anti-nutritional compounds, increased consumer health benefits) and/or (iii) an increased/facilitated ability to harvest the crop, improved processability of the crop and/or better storage stability/shelf life. Increased yield of an agricultural plant means that, where it is possible to take a quantitative measurement, the yield of a product of the respective plant is increased by a measurable amount over the yield of the same product of the plant produced under the same conditions, but without application of the present invention. According to the present invention, it is preferred that the yield be increased by at least 0.5%, more preferred at least 1%, even more preferred at least 2%, still more preferred at least 4%, preferably 5% or even more.

Any or all of the above crop enhancements may also lead to an improved utilisation of land, i.e. land which was previously unavailable or sub-optimal for cultivation may become available. For example, plants which show an increased ability to survive in drought conditions, may be able to be cultivated in areas of sub-optimal rainfall, e.g. perhaps on the fringe of a desert or even the desert itself.

In one aspect of the present invention, crop enhancements are made in the substantial absence of pressure from pests and/or diseases and/or abiotic stress. In a further aspect of the present invention, improvements in plant vigour, stress tolerance, quality and/or yield are made in the substantial absence of pressure from pests and/or diseases. For example pests and/or diseases may be controlled by a pesticidal treatment that is applied prior to, or at the same time as, the method of the present invention. In a still further aspect of the present invention, improvements in plant vigour, stress tolerance, quality and/or yield are made in the absence of pest and/or disease pressure. In a further embodiment, improvements in plant vigour, quality and/or yield are made in the absence, or substantial absence, of abiotic stress.

The compounds of the present invention can be used alone, but are generally formulated into compositions using formulation adjuvants, such as carriers, solvents and surface-active agents (SFAs). Thus, the present invention further provides a composition comprising a compound of the present invention and an agriculturally acceptable formulation adjuvant. There is also provided a composition consisting essentially of a compound of the present invention and an agriculturally acceptable formulation adjuvant. There is also provided a composition consisting of a compound of the present invention and an agriculturally acceptable formulation adjuvant.

The present invention further provides a plant growth regulator composition comprising a compound of the present invention and an agriculturally acceptable formulation adjuvant. There is also provided a plant growth regulator composition consisting essentially of a compound of the present invention and an agriculturally acceptable formulation adjuvant. There is also provided a plant growth regulator composition consisting of a compound of the present invention and an agriculturally acceptable formulation adjuvant.

The present invention further provides a plant abiotic stress management composition comprising a compound of the present invention and an agriculturally acceptable formulation adjuvant. There is also provided a plant abiotic stress management composition consisting essentially of a compound of the present invention and an agriculturally acceptable formulation adjuvant. There is also provided a plant abiotic stress management composition consisting of a compound of the present invention and an agriculturally acceptable formulation adjuvant.

The present invention further provides a seed germination promoting composition comprising a compound of the present invention and an agriculturally acceptable formulation adjuvant. There is also provided a seed germination promoting composition consisting essentially of a compound of the present invention and an agriculturally acceptable formulation adjuvant. There is also provided a seed germination promoting composition consisting of a compound of the present invention and an agriculturally acceptable formulation adjuvant.

The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The compositions generally comprise from 0.1 to 99% by weight, especially from 0.1 to 95% by weight, compounds of the present invention and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultralow volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of the present invention.

Dustable powders (DP) may be prepared by mixing a compound of the present invention with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of the present invention with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of the present invention with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of the present invention and one or more powdered solid diluents or carriers, or from preformed blank granules by absorbing a compound of the present invention (or a solution thereof, in a suitable agent) in a porous granular material (such as pumice, attapulgite clays, fullers earth, kieselguhr, diatomaceous earths or ground corn cobs) or by adsorbing a compound of the present invention (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of the present invention in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of the present invention in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of the present invention either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of the present invention is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of the present invention. SCs may be prepared by ball or bead milling the solid compound of the present invention in a suitable medium, optionally with one or more dispersing agents, to produce a fine particle suspension of the compound. One or more wetting agents may be included in the composition and a suspending agent may be included to reduce the rate at which the particles settle. Alternatively, a compound of the present invention may be dry milled and added to water, containing agents hereinbefore described, to produce the desired end product.

Aerosol formulations comprise a compound of the present invention and a suitable propellant (for example n-butane). A compound of the present invention may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of the present invention and, optionally, a carrier or diluent therefor. The polymeric shell may be produced by either an interfacial polycondensation reaction or by a coacervation procedure. The compositions may provide for controlled release of the compound of the present invention and they may be used for seed treatment. A compound of the present invention may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of the present invention. Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of the present invention). Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The compound or composition of the present invention may be applied to a plant, part of the plant, plant organ, plant propagation material or a plant growing locus.

The term "plants" refers to all physical parts of a plant, including seeds, seedlings, saplings, roots, tubers, stems, stalks, foliage, and fruits.

The term "locus" as used herein means fields in or on which plants are growing, or where seeds of cultivated plants are sown, or where seed will be placed into the soil. It includes soil, seeds, and seedlings, as well as established vegetation.

The term "plant propagation material" denotes all generative parts of a plant, for example seeds or vegetative parts of plants such as cuttings and tubers. It includes seeds in the strict sense, as well as roots, fruits, tubers, bulbs, rhizomes, and parts of plants.

The application is generally made by spraying the composition, typically by tractor mounted sprayer for large areas, but other methods such as dusting (for powders), drip or drench can also be used. Alternatively the composition may be applied in furrow or directly to a seed before or at the time of planting.

The compound or composition of the present invention may be applied pre-emergence or post-emergence. Suitably, where the composition is used to regulate the growth of crop plants or enhance the tolerance to abiotic stress, it may be applied post-emergence of the crop. Where the composition is used to promote the germination of seeds, it may be applied pre-emergence.

The present invention envisages application of the compounds or compositions of the invention to plant propagation material prior to, during, or after planting, or any combination of these.

Although active ingredients can be applied to plant propagation material in any physiological state, a common approach is to use seeds in a sufficiently durable state to incur no damage during the treatment process. Typically, seed would have been harvested from the field; removed from the plant; and separated from any cob, stalk, outer husk, and surrounding pulp or other non-seed plant material. Seed would preferably also be biologically stable to the extent that treatment would not cause biological damage to the seed. It is believed that treatment can be applied to seed at any time between seed harvest and sowing of seed including during the sowing process.

Methods for applying or treating active ingredients on to plant propagation material or to the locus of planting are known in the art and include dressing, coating, pelleting and soaking as well as nursery tray application, in furrow application, soil drenching, soil injection, drip irrigation, application through sprinklers or central pivot, or incorporation into soil (broad cast or in band). Alternatively or in addition active ingredients may be applied on a suitable substrate sown together with the plant propagation material.

The rates of application of compounds of the present invention may vary within wide limits and depend on the nature of the soil, the method of application (pre- or post-emergence; seed dressing; application to the seed furrow; no tillage application etc.), the crop plant, the prevailing climatic conditions, and other factors governed by the method of application, the time of application and the target crop. For foliar or drench application, the compounds of the present invention according to the invention are generally applied at a rate of from 1 to 2000 g/ha, especially from 5 to 1000 g/ha. For seed treatment the rate of application is generally between 0.0005 and 150 g per 100 kg of seed.

The compounds and compositions of the present invention may be applied to dicotyledonous or monocotyledonous crops. Crops of useful plants in which the composition according to the invention can be used include perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and *Zoysia* grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

Compounds of the present invention may also be used to promote the germination of seeds of non-crop plants, for example as part of an integrated weed control program. Prior to sowing a crop, compounds of the present invention may be used to promote the germination of weed seeds, so that the weeds can be controlled using a non-selective herbicide without causing phytotoxicity issues for the crop.

Normally, in the management of a crop a grower would use one or more other agronomic chemicals or biologicals in addition to the compound or composition of the present invention. There is also provided a mixture comprising a compound or composition of the present invention, and a further active ingredient.

Examples of agronomic chemicals or biologicals include pesticides, such as acaricides, bactericides, fungicides, herbicides, insecticides, nematicides, plant growth regulators, crop enhancing agents, safeners as well as plant nutrients and plant fertilizers. Examples of suitable mixing partners may be found in the Pesticide Manual, 15th edition (published by the British Crop Protection Council). Such mixtures may be applied to a plant, plant propagation material or plant growing locus either simultaneously (for example as a pre-formulated mixture or a tank mix), or sequentially in a suitable timescale. Co-application of pesticides with the present invention has the added benefit of minimising farmer time spent applying products to crops. The combination may also encompass specific plant traits incorporated into the plant using any means, for example conventional breeding or genetic modification.

The present invention also provides the use of a compound of formula (I), (II), (II-1), (II-1a), (II-1b), (III), (III-1), (III-1a) or (III-1b) or a composition comprising a compound according to formula (I), (II), (II-1), (II-1a), (II-1b), (III), (III-1), (III-1a) or (III-1b) and an agriculturally acceptable formulation adjuvant, for improving the tolerance of a plant to abiotic stress, regulating or improving the growth of a plant, promoting seed germination and/or safening a plant against phytotoxic effects of chemicals.

The present invention also provides the use of a compound, composition or mixture of the present invention, for stimulating seed germination and/or seedling emergence, for example through faster or more uniform germination or emergence.

The present invention provides the use of a compound, composition or mixture of the present invention, for improving the tolerance of a plant to abiotic stress. In one embodiment the abiotic stress is cold, salt and/or osmotic stress.

There is also provided the use of a compound, composition or mixture of the present invention, for improving the tolerance of a plant to abiotic stress, regulating or improving the growth of a plant, promoting seed germination and/or safening a plant against phytotoxic effects of chemicals.

The compounds of the invention may be made by the following methods.

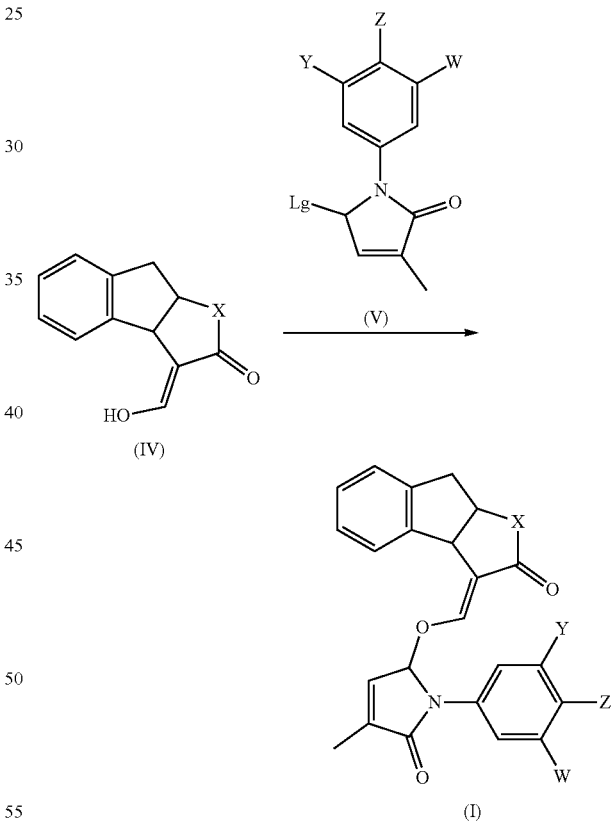

Reaction Scheme 1

Compounds of formula (I) may be prepared from compounds of formula (IV) by reaction with a compound of formula (IV) and compound (V) in the presence of a base such potassium tert-butylate or sodium tert-butylate, in the presence or not of a crown ether to activate the base. The reaction can also be carried out in the presence of a catalytic or stoichiometric amount of iodine salt, such as potassium iodide or tetrabutyl ammonium iodide. Compounds of formula (I) can be prepared by a method similar to what is described in WO2012/080115 (X=NR) and GB 1 591 374 (X=O).

Reaction Scheme 2

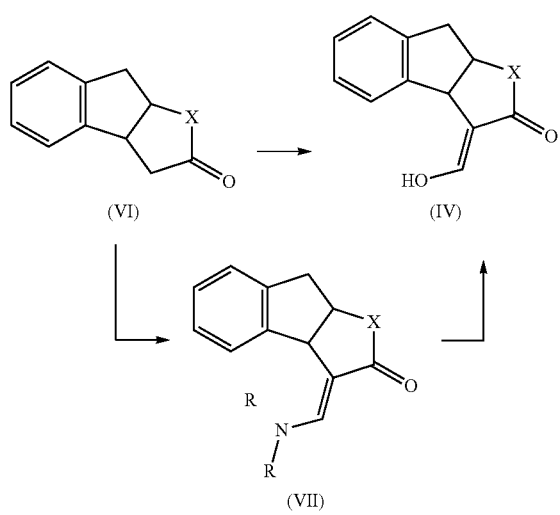

Compound of formula (IV) may be prepared from a compound of formula (VIb/c) via reaction with a formic ester derivative such as the methyl formate in presence of base such as lithium diisopropylamide, potassium tert-butylate or sodium tert-butylate, and after nitrogen substitution when X=NR[1] with R[1] being hydrogen (VIa). Alternatively, compounds of formula (IV) may be prepared from a compound of formula (VII) via hydrolysis with an acid such as hydrogen chloride. Compounds of formula (VII) may be prepared from a compound of formula (VI) via reaction with Bredereck's reagent (tert-butoxybis(dimethylamino)methane) wherein R is a methyl or analogue, and after nitrogen substitution when X=NR[1] and R[1] hydrogen. Compounds of formula (IV) can be prepared by a method similar to what is described in WO2012/080115 (X=NR[1]) and GB 1 591 374 (X=O).

Reaction Scheme 3

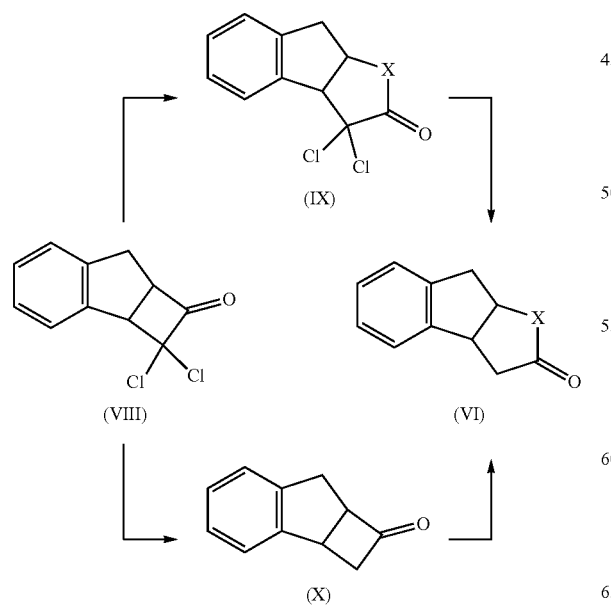

Compound of formula (VI) may be prepared from compound of formula (IX) via reduction reaction using an organic or inorganic acid such as ammonium chloride and a metal source such as Zinc. Compound of formula (IX) may be prepared from known and commercially available compound of formula (VIII) via Baeyer-Villiger reaction (X=O) using a peroxide such as Magnesium monoperoxyphthalate (MMPP) or via Beckmann reaction (X=NR[1]) using mesityl sulfonylamine (MSH) or hydroxylamine. Alternatively, compound of formula (VI) may be prepared form compound of formula (X) via Bayer-Villiger reaction (X=O) using a peroxide such as Magnesium monoperoxyphthalate (MMPP) or via Beckmann reaction (X=NR[1]) using mesityl sulfonylamine (MSH) or hydroxylamine. Compound of formula (X) may be prepared from a known and commercially available compound of formula (VII) via reduction reaction using an acid such as ammonium chloride and a metal such as Zinc

Reaction Scheme 4

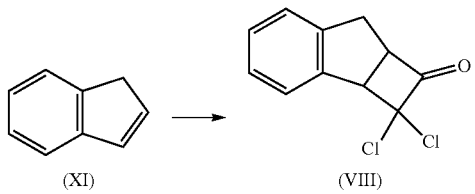

Compound of formula (VIII) may be prepared form commercially available compound of formula (XI) via [2+2] cycloaddition reaction with a ketene such as dichloroketene.

Reaction Scheme 5

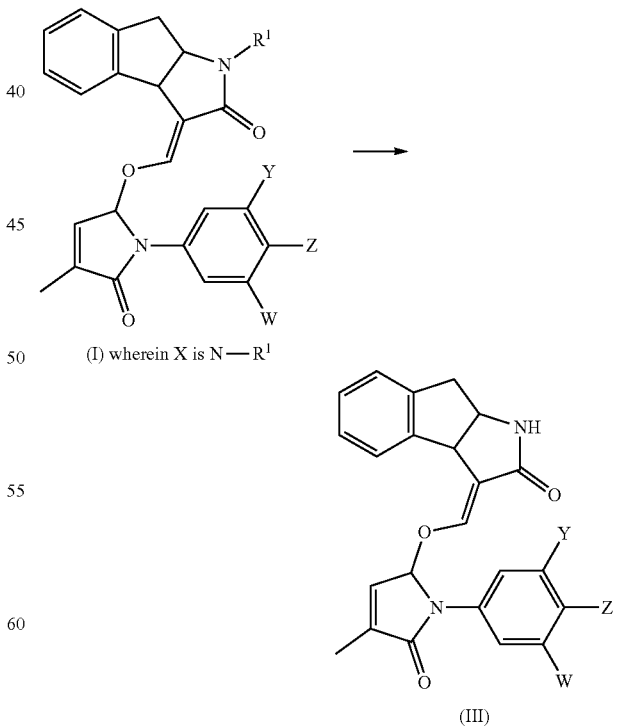

Compounds of formula (III) may be prepared from a compound of formula (I) wherein X is N—R[1], and wherein $R^1$ is an alkoxycarbonyl group such as tert-butoxycarbonyl, by reaction with an organic or inorganic acid such as trifluoroacetic acid or HCl, or in the presence of a Lewis acid such as a magnesium salt.

Reaction Scheme 6

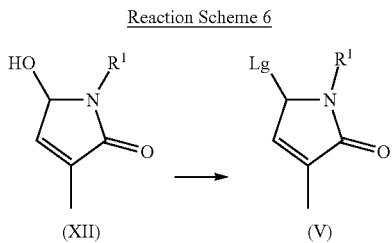

Compounds of formula (V) wherein Lg is a leaving group, such as halogen, may be prepared from compound of formula (XII) by reaction with a chlorinating agent such as thionyl chloride, phosgene or 1-chloro-N,N,2-trimethyl-1-propenylamine or a brominating agent such as $PBr_3$ or thionyl bromide, in the presence or not of a base such as pyridine.

Compounds of formula (V) wherein Lg is a leaving group such alkylsulfonyl or aryl sulfonyl may be prepared from compound of formula (XII) by reaction with the corresponding alkylsulfonyl chloride or aryl sulfonyl chloride in the presence of a base such as triethyl amine or pyridine. Compounds of formula (V) can be prepared by a method similar to what is described in WO2015/128321.

Reaction Scheme 7

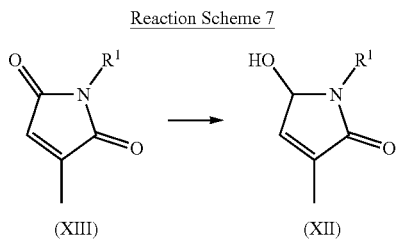

A compound of Formula (XII) may be prepared from compound of Formula (XIII) by reaction with a reducing agent such as diisopropylaluminium hydride, sodium cyanoborohydride or sodium borohydride, optionally in the presence of a Lewis acid such as cerium trichloride. Compounds of formula (XII) can be prepared by a method similar to what is described in WO2015/128321.

Reaction Scheme 8

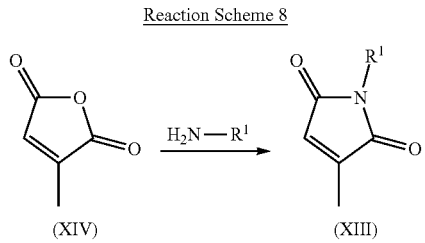

A compound of formula (XIII) may be prepared from a known and commercially available compound of formula (XIV) by reaction with an amine of formula $R^1NH_2$ or its corresponding salt by heating in an alcoholic solvent or acetic acid. Compounds of formula (XIII) can be prepared by a method similar to what is described in WO2015/128321.

PREPARATION EXAMPLES

The Examples which follow serve to illustrate the invention.
Compound Synthesis and Characterisation
The following abbreviations are used throughout this section: s=singlet; bs=broad singlet; d=doublet; dd=double doublet; dt=double triplet; bd=broad doublet; t=triplet; td=triplet doublet; bt=broad triplet; tt=triple triplet; q=quartet; m=multiplet; Me=methyl; Et=ethyl; Pr=propyl; Bu=butyl; DME=1,2-dimethoxyethane; THF=tetrahydrofuran; M.p.=melting point; RT=retention time, $MH^+$=molecular cation (i.e. measured molecular weight).

The following HPLC-MS methods were used for the analysis of the compounds:
Method A:
Spectra were recorded on a ZQ Mass Spectrometer from Waters (Single quadrupole mass spectrometer) equipped with an electrospray source (Polarity: positive or negative ions, Capillary: 3.00 kV, Cone: 30.00 V, Extractor: 2.00 V, Source Temperature: 100° C., Desolvation Temperature: 250° C., Cone Gas Flow: 50 L/Hr, Desolvation Gas Flow: 400 L/Hr, Mass range: 100 to 900 Da) and an Acquity UPLC from Waters (Solvent degasser, binary pump, heated column compartment and diode-array detector. Column: Waters UPLC HSS T3, 1.8 µm, 30×2.1 mm, Temp: 60° C., flow rate 0.85 ml/min; DAD Wavelength range (nm): 210 to 500) Solvent Gradient: A=$H_2O$+5% MeOH+0.05% HCOOH, B=Acetonitrile+0.05% HCOOH) gradient: 0 min 10% B; 0-1.2 min 100% B; 1.2-1.50 min 100% B.
Method B:
Spectra were recorded on a ZQ Mass Spectrometer from Waters (Single quadrupole mass spectrometer) equipped with an electrospray source (Polarity: positive or negative ions, Capillary: 3.00 kV, Cone: 30.00 V, Extractor: 2.00 V, Source Temperature: 100° C., Desolvation Temperature: 250° C., Cone Gas Flow: 50 L/Hr, Desolvation Gas Flow: 400 L/Hr, Mass range: 100 to 900 Da) and an Acquity UPLC from Waters (Solvent degasser, binary pump, heated column compartment and diode-array detector. Column: Waters UPLC HSS T3, 1.8 µm, 30×2.1 mm, Temp: 60° C., flow rate 0.85 ml/min; DAD Wavelength range (nm): 210 to 500) Solvent Gradient: A=$H_2O$+5% MeOH+0.05% HCOOH, B=Acetonitrile+0.05% HCOOH) gradient: 0 min 10% B; 0-2.7 min 100% B; 2.7-3.0 min 100% B.

Example P1: Preparation of 2,2-dichloro-7,7a-dihydro-2aH-cyclobuta[a]inden-1-one (VIII)

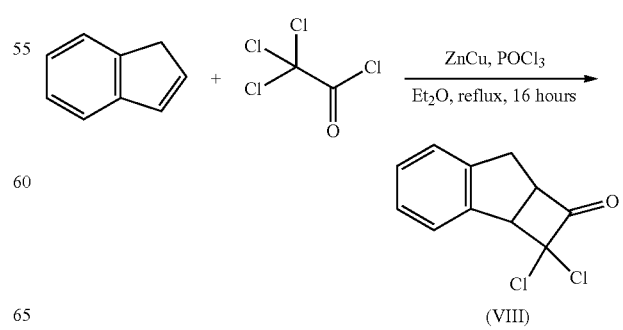

To a flask under argon was added dry diethyl ether (450 mL), indene (250 mmol, 30.1 mL) (450 ml), and cuprouszinc (751 mmol, 96.9 g). To this suspension was added a solution of trichloroacetylchloride (501 mmol, 56.5 mL) and phosphorus oxychloride (275 mmol, 25.9 mL) in diethyl ether (150 ml). After complete addition, the suspension was heated at reflux for 16 hours. The reaction mixture was then filtered through a Celite® pad which was washed with diethyl ether. The filtrate was washed with water, saturated aqueous NaHCO3 solution and brine. The organic phase was then dried over sodium sulfate, filtered, concentrated under reduced pressure and the obtained crude residue was finally purify by column chromatography on silica gel affording compound of formula (VIII) as off-white solid in 97% yield (242 mmol, 55.0 g). $^1$H NMR (400 MHz, CDCl$_3$) δ ppm 7.47 (m, 1H), 7.25-7.40 (m, 3H), 4.48-4.57 (m, 2H), 3.43 (d, 1H), 3.22 (dd, 1H).

Example P2: Preparation of 1,1-dichloro-3,3a,4,8b-tetrahydroindeno[2,1-b]pyrrol-2-one (IXa)

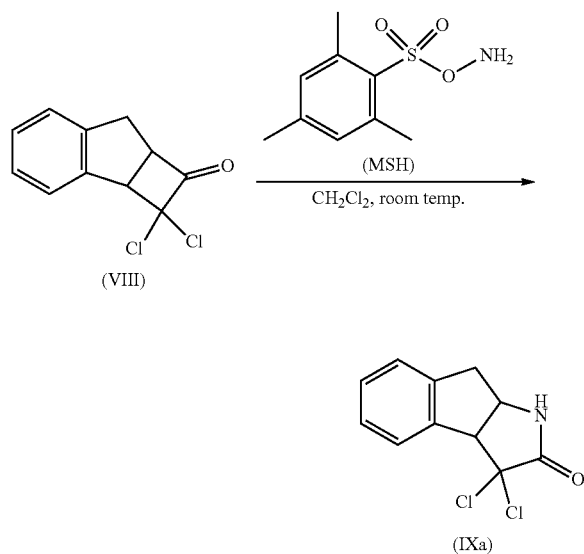

To a solution of compound of formula (VIII) (44 mmol, 10.0 g) in dichloromethane (290 mL) at room temperature was added known Mesityl Sulfonyl Hydroxylamine (MSH, 46 mmol, 9.9 g) (refer Angew. Chem. Int. Ed. 2011, 50, 4127-4132 for preparation of MSH) and a spun of Na$_2$SO$_4$. The resulting mixture was stirred at room temperature for 7 days (additional 0.5 equivalent of freshly prepared MSH was added after 4 days). The suspension was then filtered on Celite® and the filter cake was washed with dichloromethane. The filtrate was concentrated under reduced pressure (crude residue was kept in a minimum of solvent due to potential presence of residual MSH) and the crude residue was purified by flash chromatography on silica gel. Compound of formula (IXa) was isolated as a white solid in 70% yield (31 mmol, 7.5 g). LCMS (Method A): RT 0.83 min; ES+ 243 (M+H+); NMR (400 MHz, CDCl$_3$) δ ppm 7.60 (d, 1H), 7.40 (bs, 1H), 7.13-7.28 (m, 3H), 4.55 (td, 1H), 4.42 (d, 1H), 3.16 (dd, 1H), 2.98 (dd, 1H).

Example P3: Preparation of 3,3a,4,8b-tetrahydro-1H-indeno[2,1-b]pyrrol-2-one (VIa)

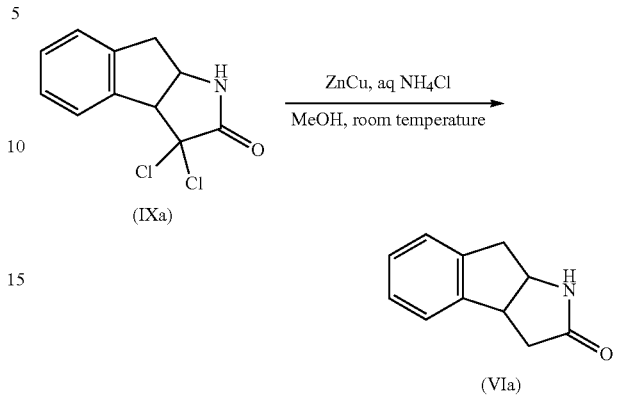

Compound of formula (IXa, 8.3 mmol, 2.0 g) was dissolved in a saturated solution of ammonium chloride (41.5 mmol, 2.2 g) in methanol (80 mL) then cuprouszinc (33.2 mmol, 4.2 g) was added and the resulting suspension was stirred at room temperature for 16 hours. The reaction mixture was then filtered on Celite®, the filter cake washed with MeOH and the filtrate was evaporated under reduced pressure to afford 3.5 g of a white residue which was suspended in EtOAc and and washed with water several times. The combined water was then re-extracted with EtOAc. The combined organic fractions were then washed with brine, dried over Na$_2$SO$_4$, filtered and concentrated under reduced pressure to afford compound of formula (VIa) as a white solid in 99% yield (8.2 mmol, 1.4 g). LCMS (Method A): RT 0.63 min; ES+ 174 (M+H+); $^1$H NMR (400 MHz, CDCl$_3$) δ ppm 7.22-7.32 (m, 4H), 6.06 (bs, 1H), 4.53 (t, 1H), 3.98 (m, 1H), 3.27 (dd, 1H), 2.99 (d, 1H), 2.90 (dd, 1H), 2.53 (d, 1H).

Example P4: Preparation of tert-butyl 2-oxo-1,3a,4,8b-tetrahydroindeno[2,1-b]pyrrole-3-carboxylate (VIb)

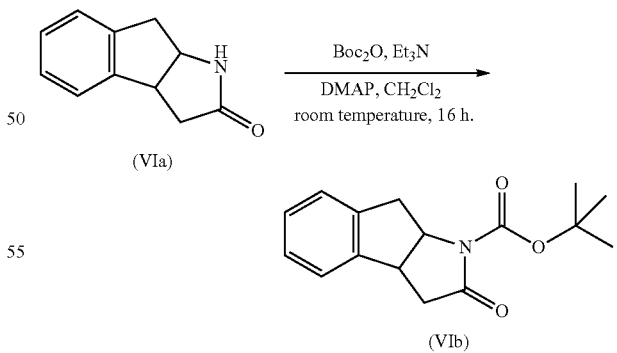

Compound of formula (VIa, 8.3 mmol, 1.4 g) was dissolved in CH$_2$Cl$_2$ (40 mL) and tert-butoxycarbonyl tert-butyl carbonate (10.0 mmol, 2.2 g), trimethylamine (16.6 mmol, 2.3 mL), N,N-dimethylpyridin-4-amine (0.41 mmol, 0.05 g) was then added the solution. The reaction mixture was stirred for 16 hours at room temperature. The medium was then washed with HCl (1M) and the aqueous layer was extracted with CH$_2$Cl$_2$. The combined organic layers were washed with a solution of NaHCO$_3$, dried over Na$_2$SO$_4$, filtered and evaporated to afford compound of formula (VIb) in quantitative yield (8.4 mmol, 2.3 gram). $^1$H NMR (400 MHz, CDCl$_3$) δ ppm 7.10-7.22 (m, 4H), 4.80 (td, 1H), 3.77 (m, 1H), 3.38 (dd, 1H), 3.11 (dd, 1H), 2.97 (dd, 1H), 2.60 (dd, 1H), 1.49 (s, 9H)

Example P5: Preparation of tert-butyl (1E)-1-(hydroxymethylene)-2-oxo-4,8b-dihydro-3aH-indeno[2,1-b]pyrrole-3-carboxylate (IVb)

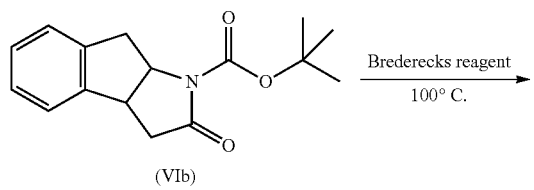

(VIb)

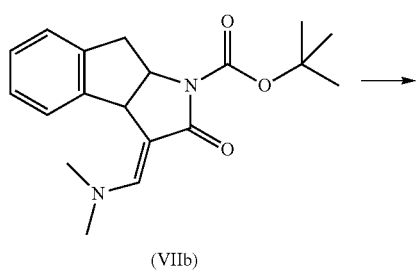

(VIIb)

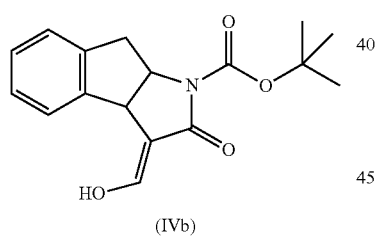

(IVb)

Compound of formula (VIb) (11.0 mmol, 3.3 g) was treated with Bredereck's reagent (tert butoxybis(dimethylamino)methane) (34 mmol, 6.7 g) under argon and the reaction mixture was heated to 100° C. (brown solution) for 1 h45 min. After cooling to room temperature, the reaction mixture was diluted with ethyl acetate (150 ml) and washed with water follow by brine, dried over Na$_2$SO$_4$ and the solvent was evaporated under reduced pressure. The crude reaction residue was then treated with pentane and the resulting solid was filtered off affording compound of formula (VIIb) in 90% yield (10.3 mmol, 3.4 g). Compound of formula (VIIb) (7.8 mmol, 2.5 g) was then dissolved in 1,4-dioxane (40.0 mL) and aqueous hydrochloric acid solution (1M, 15.5 mL) and the resulting reaction mixture was stirred for 35 minutes at room temperature. Brine was added and extraction was done with ethyl acetate. The combined organic fractions were dried over sodium sulfate, the solvents, evaporated and the resulting crude residue was purified by flash chromatography affording compound of formula (IVb) in 96% yield (7.4 mmol, 2.2 g). LCMS (Method A): RT 0.95 min; ES– 300 (M–H+); $^1$H NMR (400 MHz, CDCl$_3$) δ ppm 11.1 (bs, 1H), 7.14-7.34 (m, 4H), 4.95 (td, 1H), 4.38 (d, 1H), 3.56 (dd, 1H), 3.20 (dd, 1H), 1.61 (s, 9H).

Example P6: Preparation of tert-butyl (1E)-1-[[1-[3,5-bis(trifluoromethyl)phenyl]-4-methyl-5-oxo-2H-pyrrol-2-yl]oxymethylene]-2-oxo-4,8b-dihydro-3aH-indeno[2,1-b]pyrrole-3-carboxylate (I-1)

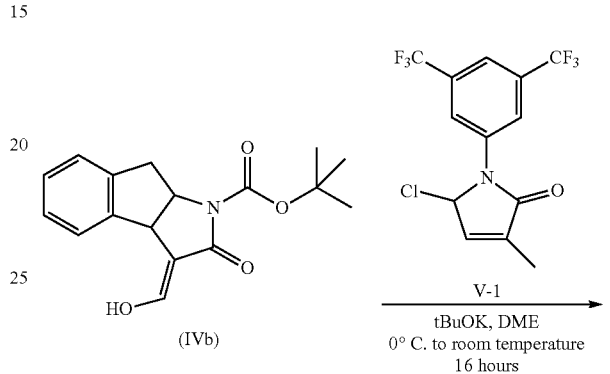

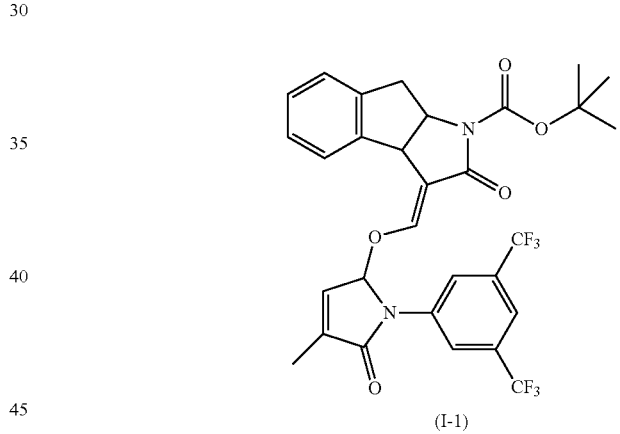

(I-1)

Compound of formula (IVb, 1.0 mmol, 0.3 g) was suspended in anhydrous 1,2-dimethoxyethane (DME, 10 mL) under argon atmosphere and at 0° C. tBuOK (1.14 mmol, 0.13 g) was introduced in one portion and after 30 minutes at 0° C., compound of formula (V-1, 1.01 mmol, 0.28 g) was added as solution in 2 mL of DME, The medium was stirred for 16 hours at room temperature, 20 ml of an aqueous NH$_4$Cl solution was added and the reaction mixture was extracted with ethyl acetate (3×30 mL). The combined organic layers were washed with brine, dried over sodium sulfate and concentrated under reduced pressure affording compound of formula (I-1) as a crude 1:1 mixture of diastereoisomer (yield assumed >99%). LCMS (Method A): RT 2.25 min; ES+ 610 (M+H+)

Compounds I-2, I-2, I-30 and I-71 were prepared following a similar procedure to that described in WO2012/080115:

(I-2)

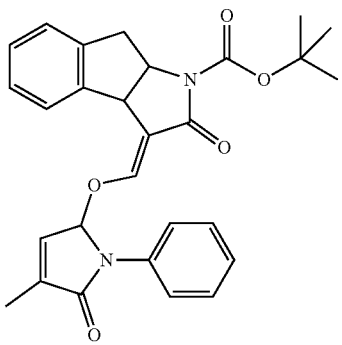

LCMS (Method A):
RT 1.13 min; ES+ 473 (M + H +)

(I-29)

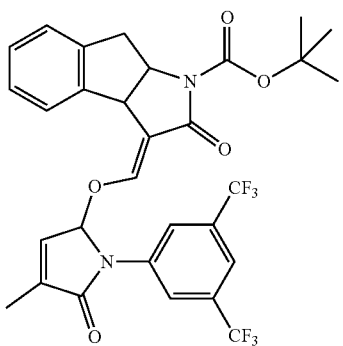

LCMS (Method A):
RT 1.31 min; ES- 621 (M - H +)

(I-30)

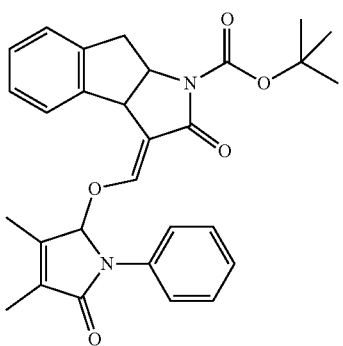

LCMS (Method B):
RT 1.95 min; ES+ 448 (M + H +)

(I-71)

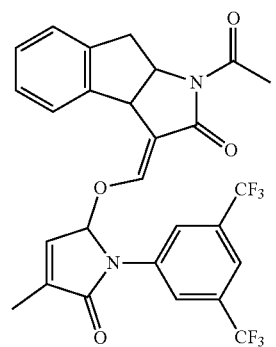

LCMS (Method A):
RT 1.20 min; ES+ 551 (M + H +)

Example P7: Preparation of (1E)-[[1-[3,5-bis(trifluoromethyl)phenyl]-4-methyl-1-oxo-2H-pyrrol-2-yl]oxymethylene]-3,3a,4,8b-tetrahydroindeno[2,1-b]pyrrol-2-one (III-1)

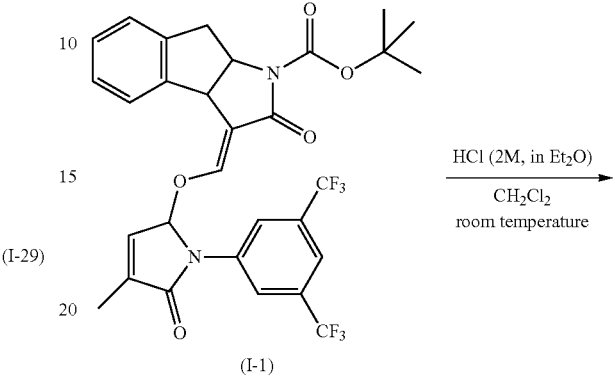

(III-1)

Compound of formula (I-1, 3.9 mmol, 2.4 g) was solved in CH$_2$Cl$_2$ (24 mL) under argon and HCl (2M in Et$_2$O, 10 mL) was added dropwise. The resulting solution was stirred for 3 hours at room temperature and then poured into an aqueous saturated NaHCO$_3$ solution (50 ml). The phases were separated, the aqueous phase extracted with CH$_2$Cl and the combined organic fractions were washed with brine, dried over NaSO$_4$ and concentrated to dryness. The resulting crude brown oil (2.1 g) brown was solved in EtOAC (5 ml) and after 2 hours at room temperature, the solid formed was collected, washed with EtOAc and dry under high vacuum. Compound of formula (III-1) was obtained as a white solid in 26% yield (1.03 mmol, 0.52 g) and as 1:1 mixture of diastereoisomer. LCMS (Method A): RT 1.11 min; ES+509 (M–H+); $^1$H NMR (400 MHz, CDCl$_3$) δ ppm (mixture of diastereoisomers) 8.33 (s, 2H), 8.30 (s, 2H), 7.73 (bs, 2H), 7.70 (bs, 2H), 7.33 (d, 1H), 7.10-7.23 (m, 5H), 6.96-7.05 (m, 2H), 6.84 (m, 2H), 6.39 (m, 1H), 6.37 (m, 1H), 5.91 (bs, 1H), 5.89 (bs, 1H), 4.64 (d, 1H), 4.52 (d, 1H), 4.43 (t, 1 h), 4.37 (t, 1H), 3.28 (m, 1H), 3.25 (m, 1H), 2.96 (m, 1H), 2.92 (m, 1H), 2.09 (m, 6H)

Compounds III-2, III-15 and III-16 were prepared following a similar procedure:

(III-2)

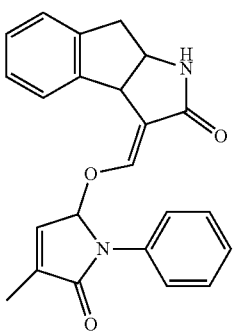

LCMS (Method A): RT 0.89 min; ES+ 373 (M+H+); 1H NMR (400 MHz, CDCl3) δ ppm (mixture of stereoisomers, data given for both diastereoisomers) 7.63 (m, 2H), 7.58 (m, 2H), 7.43 (m, 4H), 7.08-7.31 (m, 10H), 6.88 (m, 2H), 6.75 (m, 2H), 6.31 (bs, 1H), 6.28 (bs, 1H), 6.03 (bs, 2H), 4.58 (m, 1H), 4.48 (m, 1H), 4.39 (t, 1H), 4.34 (t, 1H), 3.27-3.18 (m, 2H), 2.96-2.87 (m, 2H), 2.08 (m, 3H), 2.06 (m, 3H).

(III-15)

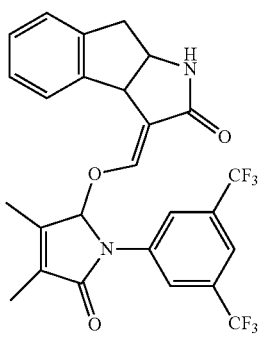

LCMS (Method A): RT 1.13 min; ES+523 (M+H+); 1H NMR (400 MHz, CDCl3) δ ppm (mixture of stereoisomers, data given for both diastereoisomers) 8.32 (bs, 2H), 8.30 (bs, 2H), 7.69 (bs, 1H), 7.66 (bs, 1H), 7.12-7.25 (m, 8H), 7.00 (m, 1H), 6.97 (m, 1H), 6.47 (bs, 1H), 6.41 (bs, 1H), 6.21 (bs, 1H), 6.18 (bs, 1H), 4.64 (m, 1H), 4.53 (m, 1H), 4.43 (m, 1H), 4.35 (m, 1H), 3.27 (m, 1H), 3.23 (m, 1H), 2.96 (m, 1H), 2.91 (m, 1H), 2.10 (bs, 3H), 2.07 (bs, 3H), 1.96 (bs, 6H).

(III-16)

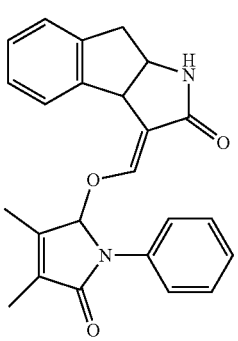

LCMS (Method A): RT 0.95 min; ES+387 (M+H+); 1H NMR (400 MHz, CDCl3) δ ppm (mixture of stereoisomers, data given for both diastereoisomers) 7.63 (m, 2H), 7.57 (m, 2H), 7.36-7.45 (m, 4H), 7.03-7.30 (m, 11H), 6.85-6.93 (m, 2H), 6.13 (bs, 1H), 6.11 (bs, 1H), 6.08 (bs, 1H), 4.60 (m, 1H), 4.51 (m, 1H), 4.40 (t, 1H), 4.35 (t, 1H), 3.18-3.27 (m, 2H), 2.88-2.97 (m, 2H), 2.06 (s, 3H), 2.04 (s, 3H), 1.96 (s, 3H), 1.94 (s, 3H).

Example P8: Preparation of 1,1-dichloro-4,8b-dihydro-3aH4-indeno[2,1-b]furan-2-one (IXc)

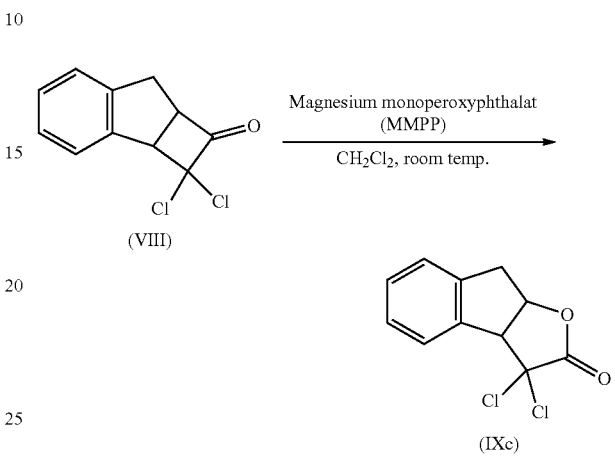

Compound of formula (VIII, 26 mmol, 6.0 g) was dissolved in methanol (88 mL) and water (50 mL), magnesium monoperoxyphtalate (66 mmol, 40.8 g) was added and the resulting solution was heated to 40-45° C. for 16 hours. After cooling to room temperature, the reaction was quenched with an aqueous solution of $Na_2S_2O_3$ (10%) follow by a saturated aqueous $NaHCO_3$ solution. The aqueous phase were extracted with EtOAc, the combine organic extracts were washed with a saturated aqueous $NaHCO_3$ solution and brine, dried over sodium sulfate and concentrated under vacuum. Compound of formula (IXc) was obtained as a light yellow solid in 79% yield (21 mmol, 5.1 g). $^1$H NMR (400 MHz, CDCl$_3$) δ ppm 7.73 (d, 1H), 7.25-7.42 (m, 3H), 5.52 (t, 1H), 4.53 (d, 1H), 3.43 (d, 1H), 3.33 (dd, 1H).

Example P9: Preparation of 3,3a,4,8b-tetrahydro-1H-indeno[2,1-b]pyrrol-2-one (VIc)

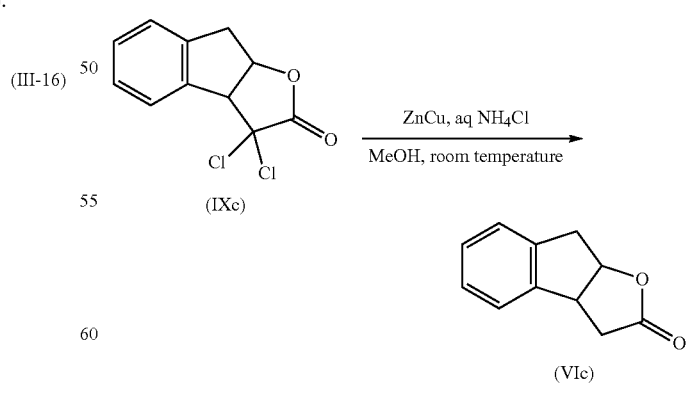

Compound of formula (IXc, 21 mmol, 5.1 g) was dissolved in a saturated solution of ammonium chloride (100 mmol, 5.6 g) in methanol (200 mL) and cuprouszinc (63 mmol, 8.1 g) was then added. The resulting reaction mixture was then stirred for 16 hours at room temperature, filtered on Celite® and the filter cake was washed with methanol. The filtrate was concentrated under vacuum and the resulting crude residue was purified by flash chromatography on silica gel. Compound of formula (VIc, 17 mmol, 2.97 mmol) was isolated as a colorless oil. LCMS (Method A): RT 0.73 min; ES+ 175 (M−H+); $^1$H NMR (400 MHz, CDCl$_3$) δ ppm 7.23-7-33 (m, 4H), 5.33 (m, 1H), 4.04 (m, 1H), 3.36 (d, 1H), 3.08 (dd, 1H), 2.77 (d, 1H).

Example P10: Preparation of (1E)-1-(hydroxymethylene)-4,8b-dihydro-3aH-indeno[2,1-b]furan-2-one (IVc)

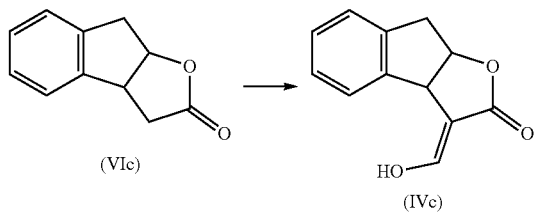 [SMILES: O=C1CC2c3ccccc3CC2O1 ; O=C1OC2Cc3ccccc3C2/C1=C\O]

Under argon, to a degassed solution of a compound of formula (VIc, 18 mmol, 3.30 g) and methylformate (54.0 mmol, 3.43 mL) in anhydrous tetrahydrofurane (120 mL) was added at 0° C. tBuOK (19.8 mmol, 2.24 g) by small portion over 5 minutes. The suspension was stirred at 0° C. for 1 hr, then allowed to reach room temperature and stirred for 16 hours. Ice-water and HCl 1M were added to the mixture (until pH~5) and the organic phase was extracted 3 times with EtOAc. The combined organic fractions were washed with brine, dried on Na$_2$SO$_4$ filtered and concentrated under vacuum. The resulting crude residue was purified by flash chromatography on silica gel and compound of formula (IVc) was isolated as an off-white solid in 74% yield (13 mmol, 2.7 g). LCMS (Method A): RT 0.74 min; ES+ 203 (M+H+); $^1$H NMR (400 MHz, CDCl$_3$) δ ppm Example P11:1-[3,5-bis(trifluoromethyl)phenyl]-4-methyl-2-[(E)-2-oxo-4,8b-dihydro-3aH-indeno[2,1-b]furan-1-ylidene)methoxy]-2H-pyrrol-5-one (II-1a/b)

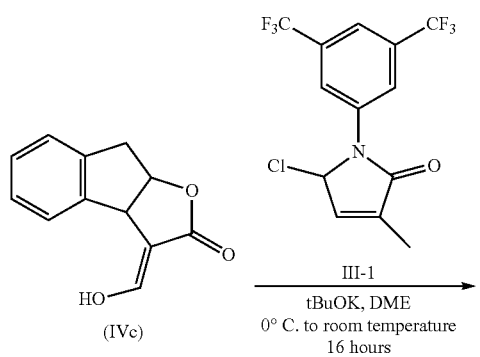

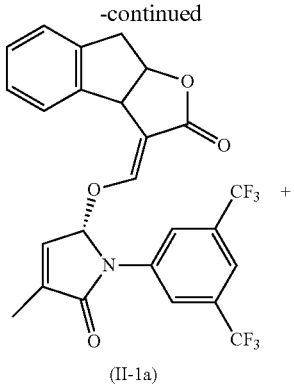

(II-1a)

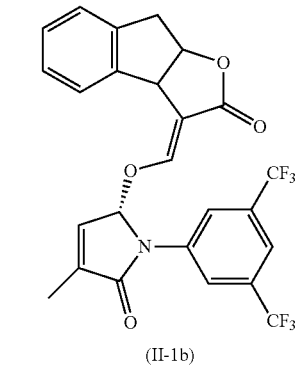

(II-1b)

Compound of formula (IVc, 0.74 mmol, 0.15 g) was dissolved in anhydrous 1,2-dimethoxyethane (DME, 7 mL), the solution cooled to 0° C. and then tBuOK (0.89 mmol, 0.10 g) was added. After 30 minutes at 0° C., a solution of compound of formula (V-1) in 3 mL of DME was added dropwise. The reaction mixture was slowly warmed to room temperature and stirred at this temperature for 72 hours. A saturated aqueous solution of NH$_4$Cl (10 ml) was then added and the aqueous phase was extracted with ethyl acetate. The combined organic extracts were washed with brine, dried over sodium sulfate and concentrated under reduced pressure. The resulting crude residue was purified by flash chromatography affording compounds of formula (II-1a, 0.078 mmol, 0.040 g) and (II-1b, 0.063 mmol, 0.032 g) (19% overall yield) as pure diastereoisomers. LCMS (Method A) for compound of formula (II-1a): RT 1.21 min; ES+ 510 (M+H+); $^1$H NMR (400 MHz, CDCl$_3$) for compound of formula (II-1a) δ ppm 8.31 (s, 2H), 7.75 (bs, 1H), 7.24-7.35 (m, 4H), 7.15-7.21 (m, 1H), 6.88 (m, 1H), 6.45 (m, 1H), 5.21 (t, 1H), 4.60 (d, 1H), 3.41 (dd, 1H), 3.32 (d, 1H), 2.13 (m, 3H). LCMS (Method A) for compound of formula (II-1b): RT 1.20 min; ES+ 510 (M+H+); $^1$H NMR (400 MHz, CDCl$_3$) for compound of formula (II-1b) δ ppm 8.29 (bs, 2H), 7.77 (bs, 1H), 7.31 (d, 1H), 7.20-7.22 (m, 2H), 7.00-7.04 (m, 2H), 6.86 (m, 1H), 6.48 (m, 1H), 5.24 (td, 1H), 4.70 (dd, 1H), 3.39 (dd, 1H), 3.31 (d, 1H), 2.14 (m, 3H).

BIOLOGICAL EXAMPLES

Comparative corn germination studies were conducted on compounds according to the invention and structurally-related compounds known from the prior art (Compounds P1 and P2 disclosed in WO2015/128321).

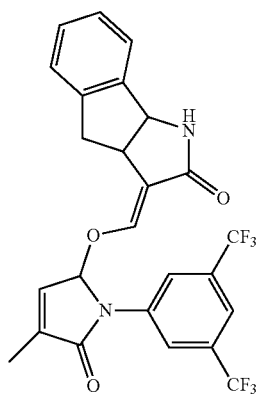

(P1)

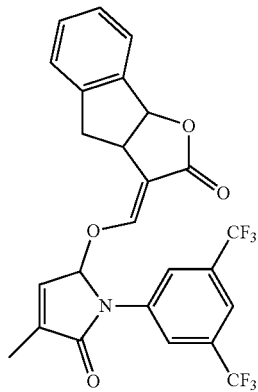

(P2)

Example B1: Corn Seed Germination—Cold Stress (15° C.)

The effect of compounds of Formula (II-1 and III-1) on the germination of NK Falkone corn seeds under salt and cold stress was evaluated as follows.

NK Falkone corn seeds (harvested in 2015) were sorted by size using a sieve to keep away round seeds.

The corn seeds were placed in 24 well plates (each plate was considered as one experimental unit or replicate). Germination was initiated by the addition of 200 µl of distilled water containing 0.5% DMSO per well. 8 replicates (i.e. 8 plates) were used for each treatment characterization. Plates were sealed using seal foil (Polyolefin Art. Nr. 900320) from HJ-BIOANALYTIK. All plates were placed in two carrousels in a climatic chamber at 15° C. The experiment was laid out in a completely randomized design in climatic chamber with 60% Relative Humidity.

Germination was followed over time by taking photographs at different time points. Image analysis was performed automatically with a macro which was developed using the Image J software. A dynamic analysis of germination was carried out by fitting a logistic curve. Three parameters were calculated from the logistic curve: the T50; the slope and the plateau. All three parameters have a high agronomical relevance and are key requirements to ensure a good early crop-establishment. The T50 and slope for a selection of compounds are outlined in Table 2 below. All the values are expressed as percentages compared to an untreated control. All the three parameters are calculated considering 8 replicates and the kinetic parameters are separately determined for each germination curve. Data in bold indicate germination enhancing statistically significant differences between treated seeds and untreated control (p<0.05). T50 corresponds to the time needed for half of the seed population to germinate. Higher negative %-values indicate faster germination. Slope indicates how synchronous the germination of the seed population is. Positive values indicate steeper curve. The steeper the curve, the better and more uniform the germination is.

TABLE 2

Effect of strigolactone analogues (II-1a/b), (III-1) and P1/2 on germination of corn seeds under cold stress condition (15° C.) at various concentrations.

| Compound | References | Rate (µM)[a] | Slope (% vs control)[b] | T50 (% vs control)[b] |
|---|---|---|---|---|
| III-1 | n/a | 0.4 | 7.3 | −0.7 |
|  |  | 2 | 14.3 | 1.3 |
|  |  | 10 | 82.6 | −8.5 |
|  |  | 50 | 175.6 | −10.1 |
| P1 | WO 2015/128321 | 0.4 | 18.4 | −2.2 |
|  |  | 2 | 7.36 | −1.4 |
|  |  | 10 | 63.91 | −8.95 |
|  |  | 50 | 144.52 | −11.7 |
| II-1a | n/a | 10 | 18.70 | −2.70 |
|  |  | 50 | 68.50 | −5.30 |
|  |  | 250 | 37.00 | −3.20 |
| II-1b | n/a | 10 | 19.20 | −2.50 |
|  |  | 50 | 41.40 | −5.10 |
|  |  | 250 | 62.40 | −5.90 |
| P2 | WO 2015/128321 | 2 | −19.5 | −0.8 |
|  |  | 10 | −13.4 | −2.0 |
|  |  | 50 | −19.7 | −0.9 |

[a]Concentration of test compound in 250 µl distilled water containing 0.5% DMSO
[b]Control = 250 µl distilled water containing 0.5% DMSO; T50 = 110 hours.

The results show that treatment of seeds with compound III-1 of the present invention leads to a higher slope (more uniform and synchronous germination) than the closest prior art compound, P1 at equivalent rates. The results also show that treatment of seeds with compound II-1a or compound II-1b of the present invention leads to a higher slope (more uniform and synchronous germination) and a lower T50 (corresponding to faster germination) than the closest prior art compound, P2 at equivalent rates.

Example B2: Corn Seed Germination—Salt (NaCl, 100 mM) and Cold Stresses (15° C.)

The effect of compounds of Formula (III-1 and P1) on the germination of NK Falkone corn seeds under salt and cold stress was evaluated as follows.

The experimental protocol was the same as in Example B1, except that germination was initiated by the addition of 200 µl of distilled water containing 0.5% DMSO and 100 mM NaCl per well. The results are shown in Table 3.

TABLE 3

Effect of strigolactone (III-1) and P1 on germination of corn seeds under cold (15° C.) and salt (NaCl) stresses condition at various concentrations.

| Compound | Rate (µM)[a] | Slope (% vs control)[b] | T50 (% vs control)[b] |
|---|---|---|---|
| III-1 | 0.4 | −4 | −0.5 |
|  | 2 | 7.4 | −1.2 |
|  | 10 | 54.1 | −9.3 |
|  | 50 | 114.7 | −6.1 |

TABLE 3-continued

Effect of strigolactone (III-1) and P1 on germination
of corn seeds under cold (15° C.)
and salt (NaCl) stresses condition at various concentrations.

| Compound | Rate ($\mu$M)[a] | Slope (% vs control)[b] | T50 (% vs control)[b] |
|---|---|---|---|
| P1 | 0.4 | 14.2 | 0.5 |
| WO 2015/128321 | 2 | 11.7 | −0.3 |
|  | 10 | 83.9 | −10.7 |
|  | 50 | 61.2 | −5.1 |

Example B3: Corn Seed Germination—Salt (NaCl, 100 mM)) Stress and Optimal Temperature (23° C.)

The experimental protocol was the same as in Example B1, except that the plates were placed in a climatic chamber at 23° C. The results are shown in Table 4.

TABLE 4

Effect of strigolactone (III-1) and P1 on germination of corn
seeds under and salt (NaCl) stress and optimal temperature
condition (23° C.) at various concentrations.

| Compound | Rate ($\mu$M)[a] | Slope (% vs control) | T50 (% vs control) |
|---|---|---|---|
| III-1 | 0.4 | 1.2 | −0.5 |
|  | 2 | −0.4 | −0.2 |
|  | 10 | 85.8 | −11 |
|  | 50 | 132.5 | −15.9 |
| P1 | 0.4 | 4.1 | −0.4 |
| WO 2015/128321 | 2 | 2.8 | 3.3 |
|  | 10 | 70.8 | −10.2 |
|  | 50 | 111.4 | −15.2 |

[a]Concentration of test compound in 250 $\mu$l distilled water containing 0.5% DMSO The results show that treatment of seeds with compound III-1 of the present invention leads to a higher slope (more uniform and synchronous germination) and a lower T50 (corresponding to faster germination) than the closest prior art compound, P1 at equivalent rates.

Example B4: Corn Seed Germination—Osmotic Stress (PEG 2%) and Cold Stresses (15° C.)

The effect of compounds of Formula (III-1 and P1) on the germination of NK Falkone corn seeds under salt and cold stress was evaluated as follows.

The experimental protocol was the same as in Example B1, except that germination was initiated by the addition of 200 $\mu$l of distilled water containing 0.5% DMSO and 2% PEG per well. The results are shown in Table 5.

TABLE 5

Effect of strigolactone (III-1) and P1 on germination of corn
seeds under osmotic (PEG 2%) and cold stresses (15° C.)
at various concentrations.

| Compound | Rate ($\mu$M)[a] | Slope (% vs control) | T50 (% vs control) |
|---|---|---|---|
| III-1 | 0.4 | 1 | 0.8 |
|  | 2 | 3.9 | −0.2 |
|  | 10 | 7.6 | −3.6 |
|  | 50 | 23.8 | −4.0 |
| P1 | 0.4 | 2.7 | −0.8 |
| WO 2015/128321 | 2 | 3.2 | −0.8 |
|  | 10 | 20.9 | −2.8 |
|  | 50 | 1.3 | −4.3 |

[a]Concentration of test compound in 250 $\mu$l distilled water containing 0.5% DMSO The results show that treatment of seeds with compound III-1 of the present invention leads to a higher slope (more uniform and synchronous germination) and a lower T50 (corresponding to faster germination) than the closest prior art compound, P1 at equivalent rates.

STABILITY EXAMPLES

Hydrolytic stability studies were conducted on compounds according to the invention and structurally-related compounds known from the prior art (Compound P1 disclosed in WO2015/128321—see above).

Example S1: Hydrolytic Stability

Sample Preparations
Standard Solutions/Treatment Solution
Prior to conducting the individual hydrolytic stability assays, stock solutions containing 1000 ppm of each test compound (i.e. compounds III-1 and P1) were prepared in acetonitrile.

The reagents used in the assays were prepared as follows. A 20 mM buffer solution was prepared from a stock solution of 20 mM mixed acetate, borate and phosphate buffer and the pH adjusted to 7 or 9 as required.

Test solutions were prepared in LC vials for each test compound in the following manner:

Hydrolytic Stability: Buffer (750 $\mu$L)+acetonitrile (250 $\mu$L)+compound stock solution (2 to 40 $\mu$L).

The buffers were initially dispensed into separate glass LC vials, placed into an autosampler complete with thermostat set at 40° C. and allowed to equilibrate for 30 minutes prior to starting the individual assays.

Analysis was carried out on Waters LCMS systems under reverse phase conditions using 10 cm C18 columns and acetonitrile (HPLC grade) acidified water (0.2% formic acid) mobile phase at a flow rate of 1 ml min-1. Peak detection was at the optimum wavelength (230-250 nm) and peak areas were used for quantification Reactions were initiated by addition of the compound solution and monitored through a series of repeat injections made directly from the vial into the HPLC system at regular time intervals. Initial and subsequent measurements of peak area attributable to the test compound were used to fit exponential half-lives and calculate first-order rate constants.

Definitive half-lives could not be determined for both detected diastereoisomers of compound III-1 (III-1a and III-1b) at pH 7 and 9 and for more polar diastereoisomer of compound P1 at pH 9, as insufficient loss was observed under the experimental conditions employed. Consequently, the percentage of compound remaining was recorded at the last assessment time.

Stability data ($t_{1/2}$), i.e. the time in hours for half of the test compound to be hydrolysed, are provided in Table 6 below.

TABLE 6

Hydrolytic stability of strigolactone analogues

| | Hydrolytic stability pH9 ($t^{1/2}$) | |
|---|---|---|
| Compound | More polar isomer (III-1a/b) [b] | Less polar isomer (III-1a/b) [b] |
| III-1 | Stable[a] | Stable[a] |
| | 94.9% remaining at 17.6 hours | 97.5% remaining at 17.6 hours |
| P1 | Stable[a] | 59 hours |
| | 97.9% remaining at 17.3 hours | 85.5% remaining at 17.3 hours |

[a] Stable = $t^{1/2}$ could not be established due to slow rate of degradation
[b] Diastereosiomers of III-1 (III-1a and III-1b) were separated on the HPLC column. Relative stereochemistry of less or polar isomers of III not determined The results show that at pH 9, the less polar isomer of compound III-1 of the present invention is more stable than the corresponding less polar isomer of the closest prior art compound, P1.

What is claimed is:

1. A compound of formula (I)

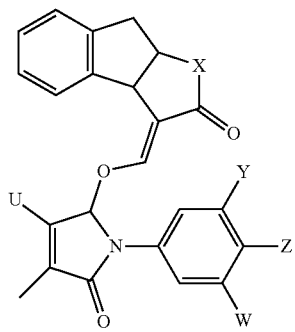

(I)

wherein X is oxygen or N—$R^1$;

$R^1$ is selected from the group consisting of hydrogen, $C_1$-$C_6$ alkyl, $C_3$-$C_6$ cycloalkyl, $C_2$-$C_6$ alkenyl, $C_2$-$C_6$ alkynyl, $C_1$-$C_8$ alkylcarbonyl, $C_1$-$C_8$ alkoxycarbonyl, aryl, heteroaryl, heterocyclyl and benzyl each optionally substituted with one or more $R^2$;

each $R^2$ is independently selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylcarbonyl, $C_1$-$C_4$ alkoxycarbonyl, carboxylic acid, aminocarbonyl, $C_1$-$C_4$ aminocarbonyl and $C_3$-$C_4$ cycloalkyl;

W, Y and Z are each independently hydrogen, methyl, trifluoromethyl or fluorine; and U is hydrogen or methyl; or salts thereof.

2. A compound according to claim 1, wherein X is N—$R^1$, and $R^1$ is selected from the group consisting of hydrogen, $C_1$-$C_6$ alkyl, $C_1$-$C_8$ alkylcarbonyl, $C_1$-$C_8$ alkoxycarbonyl and heteroaryl each optionally substituted with one or more $R^2$.

3. A compound according to claim 1, wherein $R^1$ is selected from the group consisting of hydrogen, methyl, acetyl, thiazoyl and C(O)OtBu.

4. A compound according to claim 1, wherein W and Y are independently selected from the group consisting of trifluoromethyl, fluorine and methyl, and wherein Z is fluorine or hydrogen.

5. A compound according to claim 1, wherein W and Y are $CF_3$.

6. A compound according to claim 1, wherein Z is H.

7. A compound according to claim 1, wherein U is H.

8. A compound of formula (II-1):

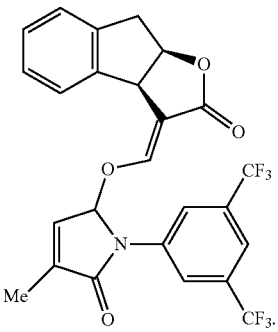

(II-1)

9. A compound selected from a compound of formula (III-1):

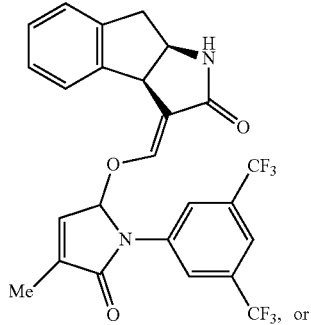

(III-1)

or a compound of formula (III-15):

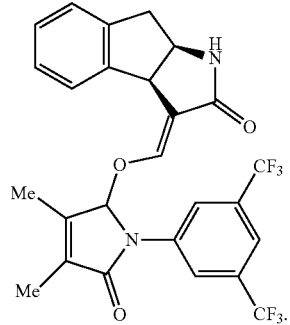

(III-15)

10. The compound of claim 9, wherein the compound is the compound of formula (III-15):

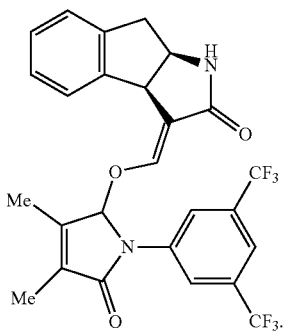
(III-15)

11. The compound of claim 9, wherein the compound is the compound of formula (III-1):

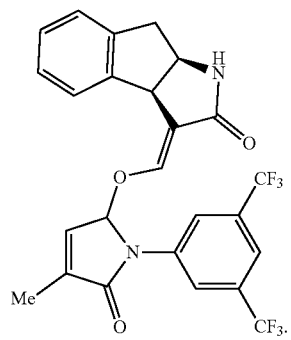
(III-1)

12. A compound according to claim 3, wherein W and Y are independently selected from the group consisting of trifluoromethyl, fluorine and methyl, and wherein Z is fluorine or hydrogen.

13. A compound according to claim 12, wherein W and Y are $CF_3$.

14. A compound according to claim 13, wherein Z is H and $R^1$ is H.

15. A composition comprising a compound according to claim 1, and an agriculturally acceptable formulation adjuvant.

16. A mixture comprising a compound as defined in claim 1, and a further active ingredient.

17. A method for promoting seed germination of a plant, wherein the method comprises applying to the plant, plant part, plant propagation material or plant growing locus a compound according claim 1.

18. A method for improving the tolerance of a plant to abiotic stress, wherein the method comprises applying to the plant, plant part, plant propagation material, or plant growing locus a compound according to claim 1.

19. A method for regulating or improving the growth of a plant, wherein the method comprises applying to the plant, plant part, plant propagation material, or plant growing locus a compound according to claim 1.

20. Plant propagation material comprising a compound according to claim 1.

* * * * *